United States Patent [19]

Lundberg, Jr. et al.

[11] 4,321,382
[45] Mar. 23, 1982

[54] 2-AMINO-11B-ARYL-BENZO[a]QUINOLI-ZINES

[75] Inventors: Charles A. Lundberg, Jr.; Robert A. Farr, both of Cincinnati, Ohio

[73] Assignee: Richardson-Merrell Inc., Wilton, Conn.

[21] Appl. No.: 65,668

[22] Filed: Aug. 10, 1979

[51] Int. Cl.$^3$ ............................................. C07D 455/06
[52] U.S. Cl. ..................................... 546/95; 424/248.4; 424/248.53; 424/248.56; 424/248.58; 424/250; 424/267; 544/126; 544/361; 546/144
[58] Field of Search .................. 546/95; 544/126, 361; 424/267, 250, 248.4, 248.54, 248.56, 248.58, 248.53

[56] References Cited

U.S. PATENT DOCUMENTS

| | | | |
|---|---|---|---|
| 3,009,918 | 11/1961 | Openshaw et al. | 546/95 |
| 3,045,021 | 7/1962 | Brossi | 546/95 X |
| 3,383,388 | 5/1968 | Houlihan et al. | 546/95 X |
| 3,452,025 | 6/1969 | Hansen et al. | 546/95 |
| 3,634,431 | 1/1972 | Van Dyke | 546/95 |
| 3,635,986 | 1/1972 | Van Dyke | 546/95 |

OTHER PUBLICATIONS

White, W., et al., *J. Org. Chem.*, 32, 213-214 (1967).
March, J., Advanced Organic Chemistry: Reactions, Mechanisms, and Structure, McGraw Hill, New York, 1968, pp. 465 and 715.
Ichiya, N., et al., *Heterocycles*, 3(4), 307 (1975).

*Primary Examiner*—Richard A. Schwartz
*Attorney, Agent, or Firm*—John J. Kolano; Raymond A. McDonald; Gary D. Street

[57] ABSTRACT

Compounds of the formula

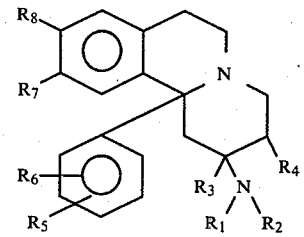

wherein
$R_1$ is hydrogen, a straight or branched chain alkyl of 1-5 carbon atoms or a straight or branched chain alkanoyl of 1-5 carbon atoms;
$R_2$ is hydrogen, a straight or branched chain alkyl of 1-5 carbon atoms, phenyl, phenyl substituted with halogen, a straight or branched chain alkoxy of 1-5 carbon atoms, a straight or branched chain alkyl of 1-5 carbon atoms or trifluoromethyl or, when $R_1$ is hydrogen, $R_2$ can also be a straight or branched chain alkanoyl of 1-5 carbon atoms; or
$R_1$ and $R_2$ taken together with the nitrogen atom to which they are attached form a saturated heterocyclic ring of 4-7 total ring atoms and 0 or 1 hetero N or O atom in addition to the connecting N atom; or the corresponding heterocyclic ring substituted by a $C_{1-5}$ straight or branched chain alkyl group, aryl or aralkyl;
$R_3$ is hydrogen, primary or secondary alkyl of 1-5 carbon atoms, phenyl or phenyl substituted by halogen, a straight or branched chain alkoxy of 1-5 carbon atoms, a straight or branched chain alkyl of 1-5 carbon atoms or trifluoromethyl;
$R_4$ is hydrogen or a straight or branched chain alkyl of 1-5 carbon atoms;
each of $R_5$ and $R_6$ is, independently, hydrogen, halogen, a straight or branched chain alkyl of 1-5 carbon atoms, a straight or branched chain alkoxy of 1-5 carbon atoms, trifluoromethyl, a $C_{3-6}$ alkyleneimino attached via the nitrogen atom and optionally substituted by a straight or branched chain $C_{1-5}$ alkyl, or NR'R'' wherein each of R' and R'' is, independently, hydrogen or a straight or branched chain alkyl of 1-5 carbon atoms; and
each of $R_7$ and $R_8$ is, independently, hydrogen, halogen, a straight or branched chain alkyl of 1-5 carbon atoms, a straight or branched chain alkoxy of 1-5 carbon atoms, hydroxy, carboxy or phenyl;
and the pharmaceutically acceptable acid addition salts thereof;
are useful as antisecretory, antiinflammatory, antihistaminic, antiallergenic, antiseritonin, anticonvulsant and analgesic agents.

2 Claims, No Drawings

2-AMINO-11B-ARYL-BENZO[a]QUINOLIZINES

BACKGROUND OF THE INVENTION

The present invention relates to 2-substituted-11b-aryl-benzo[a]quinolizines and their pharmaceutically acceptable acid addition salts, as well as the individual optical and geometric isomers thereof, which are pharmacologically active.

11b-Aryl-benzo[a]quinolizines are known. (Kametani et al, J. Heterocyclic Chem., 11, 1023 (1974); Ichiya et al, Heterocycles, 3, 307 (1975); and U.S. Pat. Nos. 3,383,388 and 3,583,976.) However, none of these has substituents in the 2-position.

SUMMARY OF THE INVENTION

This invention is directed to pharmacologically active 11b-aryl-benzo[a]quinolizine-2-amines of Formula I

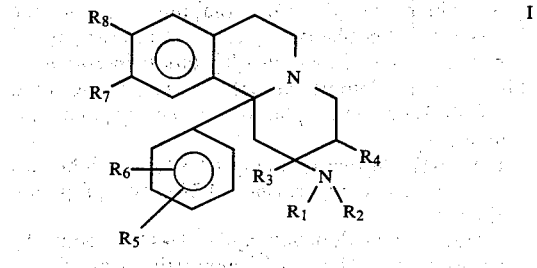

wherein $R_1$ is hydrogen, a straight or branched chain alkyl of 1-5 carbon atoms or a straight or branched chain alkanoyl of 1-5 carbon atoms;

$R_2$ is hydrogen, a straight or branched chain alkyl of 1-5 carbon atoms, phenyl which can be optionally substituted at the ortho, meta or para position with, for example, halogen, a straight or branched chain alkoxy of 1-5 carbon atoms, a straight or branched chain alkyl of 1-5 carbon atoms or trifluoromethyl or, when $R_1$ is hydrogen, $R_2$ can also be a straight or branched chain alkanoyl of 1-5 carbon atoms; or $R_1$ and $R_2$ taken together with the nitrogen atom to which they are attached form a saturated, optionally substituted, heterocyclic ring, e.g., of 4-7 total ring atoms and 0 or 1 hetero N or O atom in addition to the connecting N atom; or the corresponding heterocyclic ring substituted by a $C_{1-5}$ straight or branched chain alkyl group, for example, azetidine, pyrrolidine, piperidine, hexahydroazepine, morpholine or piperazine which can be optionally substituted with a straight or branched chain alkyl of 1-5 carbon atoms, aryl or aralkyl, e.g., phenyl or benzyl;

$R_3$ is hydrogen, primary or secondary alkyl of 1-5 carbon atoms or phenyl which can optionally be substituted in the ortho, meta or para position with, for example, halogen, a straight or branched chain alkoxy of 1-5 carbon atoms, a straight or branched chain alkyl of 1-5 carbon atoms or trifluoromethyl;

$R_4$ is hydrogen or a straight or branched chain alkyl of 1-5 carbon atoms;

each of $R_5$ and $R_6$ is, independently, hydrogen, halogen, a straight or branched chain alkyl of 1-5 carbon atoms, a straight or branched chain alkoxy of 1-5 carbon atoms, trifluoromethyl, a saturated, optionally substituted, nitrogen containing heterocyclic ring which is attached via the nitrogen atom, e.g., a $C_3$-$C_6$ alkylenimino attached via the nitrogen atom and optionally substituted by a straight or branched chain $C_{1-5}$ alkyl, such as, for example, azetidine, pyrrolidine, piperidine or hexahydroazepine or —NR'R" wherein each R' and R" is, independently, either hydrogen or a straight or branched chain alkyl of 1-5 carbon atoms; and each of $R_7$ and $R_8$ is, independently, hydrogen, halogen, a straight or branched chain alkyl of 1-5 carbon atoms, a straight or branched chain alkoxy of 1-5 carbon atoms, hydroxy, phenyl or carboxy;

and their pharmaceutically acceptable acid addition salts including their individual optical and geometric isomers (e.g., in the 2-position).

These compounds are useful as antisecretory, antiinflammatory, antihistaminic, antiallergenic, antiseritonin, anticonvulsant and analgesic agents.

Furthermore, 11b-aryl-benzo[a]quinolizines of the formula II

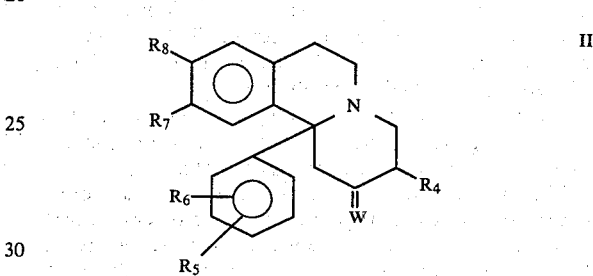

wherein $R_4$-$R_8$ are as hereinabove defined and W is oxygen, =NOH or =NR''', wherein R''' is hydrogen, a straight or branched chain alkyl of 1-5 carbon atoms or phenyl which can be optionally substituted at the ortho, meta, or para position with, for example, halogen, a straight or branched chain alkyl of 1-5 carbon atoms, a straight or branched chain alkoxy of 1-5 carbon atoms or trifluoromethyl, are useful as chemical intermediates to compounds of pharmaceutical interest.

DETAILED DESCRIPTION OF THE INVENTION

Illustrative examples of straight or branched chain alkyl groups which $R_1$, $R_2$, $R_3$, $R_4$, $R_5$, $R_6$, $R_7$, $R_8$ and R''' may represent as used herein include, for example, methyl, ethyl, n-propyl, isopropyl, n-butyl, isobutyl, pentyl, and isopentyl.

Illustrative examples of straight or branched chain alkanoyl groups which $R_1$ and $R_2$ may represent as used herein include, for example, formyl, acetyl, propionyl, butyryl, isobutyryl, valeryl and isovaleryl.

Illustrative examples of substituents for the phenyl groups represented herein by $R_2$, $R_3$ and R''' include: for halogen, F, Cl, Br and I, especially Cl and Br; for the straight or branched chain alkoxy, methoxy, ethoxy, propoxy, isopropoxy, butoxy, isobutoxy, tert-butoxy, pentoxy, isopentoxy and neopentoxy; and for straight or branched chain alkyl, those mentioned above. Substitution on all phenyl rings is preferably in the p-position. Monosubstitution is preferred.

Illustrative examples of the saturated, optionally substituted, heterocyclic ring formed when $R_1$ and $R_2$ are taken together with the nitrogen atom to which they are attached, for example, have from 4-7 ring atoms and 0 or 1 hetero N or O atom in addition to the N atom to which $R_1$ and $R_2$ are attached, such as, acetidine, pyrrolidine, piperidine, hexahydroazepine, morpholine or piperazine. Suitable substituents for these hetero rings include the $C_{1-5}$ straight or branched chain alkyl groups mentioned above. For the 6-membered rings, these substituents are preferably in the 4-position, e.g., 4-alkyl-piperazine, 4-aryl-and 4-aralkyl piperazine wherein alkyl is of 1–5 carbon atoms, preferably 1, and aryl is carbocyclic of 6–10 carbon atoms, e.g., phenyl or tolyl.

$R_5$ and $R_6$ may be attached in the o-, m- or p-positions. Preferably, one of $R_5$ and $R_6$ is other than H and, preferably, that group is in the p-position.

Illustrative examples of halogen and alkoxy which $R_5$, $R_6$, $R_7$ and $R_8$ may represent as used herein include, for example, those mentioned above as substituents for the phenyl groups represented by $R_2$, $R_3$ and $R'''$.

Illustrative examples of the saturated, optionally substituted, nitrogen-containing heterocyclic rings which $R_5$ and $R_6$ may represent as used herein, for example, are $C_{3-6}$ alkyleneimino groups such as azetidine, pyrrolidine, piperidine or hexahydroazepine. Suitable substituents on such rings include the aforementioned $C_{1-5}$ straight or branched chain alkyl groups.

Illustrative examples of straight or branched chain $C_{1-5}$ alkyl groups which $R'$ and $R''$ may represent as used herein include those mentioned above.

Pharmaceutically acceptable acid addition salts of the compounds of Formula I include those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic and 2-phenoxybenzoic, or sulfonic acids such as, for example, methanesulfonic and 2-hydroxyethane-sulfonic acid.

Of the compounds of Formula I, those wherein $R_3$, $R_4$, $R_6$, $R_7$ and $R_8$ are H; $R_5$ is H or 4-F, especially F; and/or $_1$ and $R_2$ are H or alkyl, preferably —$CH_3$, and especially both are —$CH_3$, or together form a pyrrolidine ring, are preferred. 11b-(4-Fluorophenyl)-1,3,4,6,7,11b-hexahydro-N,N-dimethyl-2H-benzo[a]quinolizin-2-amine is particularly preferred.

Illustrative examples of compounds of this invenntion are:

11b-(3,4-dichlorophenyl)-1,3,4,6,7,11b-hexahydro-N,N-dimethyl-2H-benzo[a]quinolizin-2-amine;
11b-(3,4-dichlorophenyl)-1,3,4,6,7,11b-hexahydro-N,N-dimethyl-2H-benzo[a]quinolizin-2-amine dihydrochloride;
1,3,4,6,7,11b-hexahydro-N,N-dimethyl-11b-phenyl-2H-benzo[a]quinolizin-2-amine dihydrochloride;
1,3,4,6,7,11b-hexahydro-N,N-dimethyl-11b-(4-methylphenyl)-2H-benzo[a]quinolizin-2-amine dihydrochloride monohydrate;
1,3,4,6,7,11b-hexahydro-N,N-dimethyl-11b-(4-methylphenyl)-2H-benzo[a]quinolizin-2-amine dihydrochloride;
1,3,4,6,7,11b-hexahydro-11b-(4-methylphenyl)-2-pyrrolidin-1-yl-2H-benzo[a]quinolizine dihydrochloride hemihydrate;
1,3,4,6,7,11b-hexahydro-11b-(4-methylphenyl)-2-pyrrolidin-1-yl-2H-benzo[a]quinolizine dihydrochloride;
11b-(4-chlorophenyl)-1,3,4,6,7,11b-hexahydro-2-pyrrolidin-1-yl-2H-benzo[a]quinolizine dihydrochloride;
11b-(4-fluorophenyl)-1,3,4,6,7,11b-hexahydro-2-pyrrolidin-1-yl-2H-benzo[a]quinolizine dihydrochloride;
11b-(4-fluorophenyl)-1,3,4,6,7,11b-hexahydro-2-pyrrolidin-1-yl-2H-benzo[a]quinolizine dihydrochloride monohydrate;
11b-(4-chlorophenyl)-1,3,4,6,7,11b-hexahydro-N,N-dimethyl-2H-benzo[a]quinolizine-2-amine dihydrochloride;
11b-(4-fluorophenyl)-1,3,4,6,7,11b-hexahydro-N,N-dimethyl-2H-benzo[a]quinolizin-2-amine dihydrochloride;
11b-(4-fluorophenyl)-1,3,4,6,7,11b-hexahydro-N-methyl-2H-benzo[a]quinolizin-2-amine;
11b-(4-fluorophenyl)-1,3,4,6,7,11b-hexahydro-2H-benzo[a]quinolizin-2-amine;
11b-(4-methylphenyl)-1,3,4,6,7,11b-hexahydro-2-pyrrolidin-1-yl-2H-benzo[a]quinolizine hydrochloride;
11b-(4-methoxyphenyl)-1,3,4,6,7,11b-hexahydro-N-phenyl-2H-benzo[a]quinolizin-2-amine;
11b-(4-trifluoromethylphenyl)-1,3,4,6,7,11b-hexahydro-N-p-chlorophenyl-2H-benzo[a]quinolizin-2-amine;
11b-(4-piperidinophenyl)-1,3,4,6,7,11b-hexahydro-N-p-methoxy-phenyl-2H-benzo[a]quinolizin-2-amine;
11b-(4-dimethylaminophenyl)-1,3,4,6,7,11b-hexahydro-N-p-trifluoromethylphenyl-2H-benzo[a]quinolizin-2-amine;
3-methyl-11b-(4-methylphenyl)-1,3,4,6,7,11b-hexahydro-2-p-methyl-piperazin-1-yl-2H-benzo[a]quinolizine;
10-chloro-11b-(4-fluorophenyl)-1,3,4,6,7,11b-hexahydro-N-acetyl-2H-benzo[a]quinolizin-2-amine;
9-methyl-11b-(4-fluorophenyl)-1,3,4,6,7,11b-hexahydro-N,N-dimethyl-2H-benzo[a]quinolizin-2-amine;
10-methoxy-11b-(4-fluorophenyl)-1,3,4,6,7,11b-hexahydro-N,N-dimethyl-2H-benzo[a]quinolizin-2-amine;
10-hydroxy-11b-(4-fluorophenyl)-1,3,4,6,7,11b-hexahydro-N,N-dimethyl-2H-benzo[a]quinolizin-2-amine;
9-phenyl-11b-(4-fluorophenyl)-1,3,4,6,7,11b-hexahydro-N,N-dimethyl-2H-benzo[a]quinolizin-2-amine;
9-carboxy-11b-(4-fluorophenyl)-1,3,4,6,7,11b-hexahydro-N,N-dimethyl-2H-benzo[a]quinolizin-2-amine;
and the hydrochloride salts of the above free amines.

The compounds of this invention are useful as antisecretory, antiinflammatory, antihistaminic, antiallergenic, antiserotonin, anticonvulsant and analgesic agents. They can be administered to warm-blooded animals, including mammals, e.g., humans. As used herein, the term patient is intended to mean the animal or mammal being treated. To illustrate the efficacy of the compounds of this invention for the above-mentioned uses, fully conventional pharmacological screening tests may be employed. For example, antiallergenic, antihistaminic and antiserotonin efficacy can be demonstrated by reduction in the diameter of wheal formation in rats or guinea pigs after injection of antigen (rat passive cutaneous anaphylaxis test); anticonvulsant efficacy may be demonstrated by inhibition of clonic seizures induced by injection of metrazole in mice (metrazole antagonism test); and analgesic efficacy may be demonstrated by inhibition of writhing or squirming upon administration of glacial acetic acid in mice (antagonism of acetic acid writhing test) or by an increase in the reaction time for tail withdrawal after application of radiant heat in rats (rat tail flick test).

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules and pills or liquid solutions, suspensions or emulsions for oral and parenteral administration. The dosage unit administered can be any amount effective for the intended utility mentioned above.

Total daily doses of a compound of this invention can be 10-250 mg as an antisecretory agent, 5-200 mg as an antiinflammatory agent, 0.1-100 mg as an atihistaminic agent, an antiallergenic agent or an antiserotonin agent and 5-500 mg as an anticonvulsant or as an analgesic. Unit dosages can be correspondingly selected in accordance with the frequency of administration, e.g., 1-4 times daily.

The 11b-phenyl-benzo[a]quinolizin-2-amines of Formula I can be prepared from the appropriate 11b-phenyl-benzo[a]quinolizin-2-ones of Formula II wherein W is oxygen by employing any of the well-known procedures for converting ketones to amines. For example, the corresponding ketone may be reacted with an amine of the formula

in the presence of titanium tetrachloride. Suitable reaction conditions can be conventionally selected, e.g., in accordance with the disclosure of White et al, J. Org. Chem. 32, 213 (1967). The reaction is generally carried out in the presence of a solvent, e.g., an ethereal solvent such as, for example, diethyl ether, tetrahydrofuran and the like; or an aromatic solvent such as, for example, benzene, toluene, xylene and the like. The resultant product is then conventionally reduced, e.g., by conventional hydrogenation over a catalyst, e.g., platinum, or with $NaBH_4$.

Alternatively, the corresponding ketone may be reacted with an amine of the formula

in the presence of $NaBH_3CN$, and, optionally, also in the presence of the corresponding amine hydrochloride. Suitable reaction conditions can be conventionally selected, e.g., in accordance with the disclosure of C. F. Lane, Synthesis, p. 135 (1975). This reaction is also generally carried out in the presence of a solvent. Suitable solvents include lower alcohols, such as, for example, methanol, ethanol, n-propanol, isopropanol, n-butanol and the like. The reaction time may vary from about 7 to about 15 days, depending upon the reactants, the solvent and the reaction temperature which generally is around room temperature.

Alternatively, the 11b-phenyl-benzo[a]quinolizin-2-non-cyclicamines can be prepared by reacting the compounds of general Formula II wherein W is =NOH or =NR''' with a reducing agent to form compounds of general Formula I wherein $R_1$ and $R_2$ are each hydrogen or one is hydrogen and the other is R'''. Suitable reductions which may be employed are fully conventional, e.g., reduction via $NaBH_4$, $LiAlH$, $NaBH_3CN$ or $H_2$ and a catalyst such as Pt. The resultant amines may optionally be converted to secondary or tertiary amines by employing any of the well-known methods for substituting amines. For example, these amines may be reacted at a temperature of 0°-100° C. for about 24-1 hour, normally without a solvent, with the appropriate alkyl carboxylic acid.

Those compounds of this invention wherein $R_3$ is not H can also be prepared using fully conventional methods. For example, such compounds wherein the 2-amino group is either cyclic or non-cyclic, can be prepared by reaction of the desired ketone of Formula II (W=O) with the appropriate secondary amine to form the corresponding enamine. The conditions for this step are as described above. The resultant enamine is then converted to its perchlorate salt, e.g., by reaction with perchloric acid. The latter salt is converted to a compound of Formula I wherein $R_3$ is not H by reaction of the latter salt with the appropriate $R_3$ Grignard reagent or $R_3$(alkyl)Li reagent.

Alternatively, compounds of Formula I wherein $R_3$ is not H and the 2-amino group is non-cyclic may be prepared by first reacting the appropriate ketone of Formula II (W=O) with an $R_3$Grignard or $R_3$Li reagent to form the corresponding 2-$R_3$,2-OH compound. This alcohol is then subjected to a Ritter reaction in the presence of concentrated $H_2SO_4$ and RCN(R=alkyl) to form the corresponding 2-$R_3$,2-NHCOR compound. The conditions for this reaction are fully conventional and may be selected in accordance with the disclosure, e.g., of Krimen et al, Organic Reactions, Vol. 17, (1969), p. 213 and references cited therein. The product of this reaction is then subsequently conventionally reduced e.g., with $LiAlH_4$, and the amine produced, if necessary, is subjected to conventional alkylation.

The compounds of general Formula II wherein W is oxygen can be prepared by reacting a 1-phenyl-3,4-dihydroisoquinoline (e.g., its hydrochloride) of Formula III

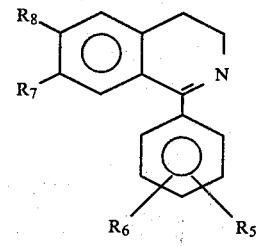

wherein $R_5$, $R_6$, $R_7$ and $R_8$ are as hereinabove defined, with about 1 to about 10 molar equivalents of a methyl vinyl ketone of Formula IV

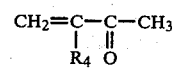

wherein $R_4$ is as hereinabove defined. This reaction may be carried out with or without a solvent. Preferably, the methyl vinyl ketone is the solvent. Suitable solvents for this reaction if desired are lower alcohols, such as methanol, ethanol, isopropanol, n-propanol, n-butanol and the like; dimethylformamide, dimethylsulfoxide; ethereal solvents, such as, for example, diethyl ether, tetrahydrofuran and the like; aromatic solvents, such as, for example, benzene, toluene, xylene and the like; and halogenated hydrocarbon solvents, such as, for example, chloroform, methylene chloride, carbon tetrachloride and the like. The reaction may be carried out in the presence of an acid catalyst such as hydrochloric acid or p-toluenesulfonic acid, preferably using one equivalent of the acid catalyst. The reaction time may vary from about 1 hour to about 10 hours, preferably about 5 hours, depending upon the reactants, the solvent if any and the reaction temperature which may vary from about 25° C. to about 150° C. The product obtained on work-up may be isolated as the free base or as the acid addition salt.

The compounds of general formula II wherein W is =NOH can be prepared by reacting an 11b-phenylbenzo[a]quinolizin-2-one of general formula II wherein W is oxygen with about 1 to about 10 molar equivalents, preferably about 2 equivalents of hydroxylamine hydrochloride in a solvent. Suitable solvents for this reaction are lower alcohols, such as, for example, methanol, ethanol, n-propanol, isopropanol, n-butanol and the like; dimethylformamide, dimethylsulfoxide; and halogenated hydrocarbon solvents, such as, for example, chloroform, methylene chloride, carbon tetrachloride and the like. The reaction time may vary from about 1 hour to about 10 hours, preferably about 5 hours, depending upon the reactants, the solvent and the reaction temperature which may vary from about 25° C. to about 150° C. The product obtained upon basic work-up may be isolated as the free base or as the acid addition salt.

The compounds of general Formula II wherein W is =NR''' can be prepared by reacting the corresponding ketone of Formula II wherein W is oxygen with $H_2NR'''$ in the presence of $TiCl_4$ utilizing the reaction conditions mentioned above for such $TiCl_4$ reactions.

The 1-phenyl-3,4-dihydroisoquinolines of general formula III are either known or can be made by methods well recognized in the art. See, for example, Organic Reactions, 6, 74 (1951). Also, the substituted methyl vinyl ketones of general Formula IV are either known or can be made by methods well recognized in the art. See, for example, Organic Reactions, 16, 1 (1968).

The following specific examples are illustrative of the invention.

EXAMPLE 1

Preparation of starting material:
11b-(4-fluorophenyl)-1,3,4,6,7,11b-hexahydro-2H-benzo[a]quinolizin-2-one 31.9 g (0.142 mole) of 1-(4-F-phenyl)-3,4-dihydroisoquinoline is converted to the hydrochloride by treatment with HCl in diethyl ether. The product is then suspended in 90 ml of methyl vinyl ketone and the reaction mixture is stirred at reflux for about 17 hours. After about 3½ hours, almost all of the hydrochloride is dissolved. The solution is filtered to give a white solid which is dissolved in water. The filtrate is concentrated in vacuo to remove most of the methyl vinyl ketone. The residue is partitioned between the ether phase and the water phase containing the dissolved solid. The ether layer is extracted with very dilute HCl and the aqueous layers are combined. $NH_4OH$ is added dropwise with stirring until the pH is about 9. A light green solid crystallizes out. Stirring is continued for about ½ hour. The solid is then collected, washed with water and dried in a vacuum oven producing 37 g of beige 11b-(4-fluorophenyl)-1,3,4,6,7,11b-hexahydro-2H-benzo[a]quinolizin-2-one. The product is then recrystallized from hexane to yield 31.8 g (76%) of beige crysals. m.p. 127.5°–130° C.

EXAMPLE 2

11b-(4-fluorophenyl)-1,3,4,6,7,11b-hexahydro-2H-benzo[a]quinolizin-2-amine 9.9 g (31.8 mmole) of 11b-(4-fluorophenyl)-1,3,4,6,7,11b-hexahydro-2H-benzo[a]quinolizin-2-oxime is dissolved in about 250 ml of hot THF-dioxane (about 3:1) and 4.0 g (105 mmole) of $LiAlH_4$ is added in 0.6 g portions over about 0.5 hour. The reaction mixture is heated at reflux overnight before a conventional $LiAlH_4$ work-up. After drying using $MgSO_4$ and concentration in vacuo 8.8 g (93%) of 11b-(4-fluorophenyl)-1,3,4,6,7,11b-hexahydro-2H-benzo[a]quinolizin-2-amine are obtained.

EXAMPLE 3

11b-(4-fluorophenyl)-1,3,4,6,7,11b-hexahydro-N,N-dimethyl-2H-benzo[a]quinolizin-2-amine dihydrochloride 8.8 g (29.7 mmole) of 11b-(4-fluorophenyl)-1,3,4,6,7,11b-hexahydro-2H-benzo[a]quinolizin-2-amine is dissolved in 8.0 g of 88% $HCO_2H$ (153 mmoles). 5.7 ml (0.4 g HCHO/ml, 75.3 mmole) of 37% HCHO is then added. The reaction mixture is heated briefly on a steam bath and then allowed to stand at 25° C. for about ½ hour as fairly rapid $CO_2$ evolution occurs. The reaction mixture is then heated overnight on a steam bath. After cooling, the mixture is diluted with water (with addition of some HCl to assure that the solution is strongly acidic), and is then washed with ether. The aqueous layer is made basic with NaOH and extracted with ether. The organic extract is washed with brine, dried ($MgSO_4$) and concentrated to give 5.7 g (60%) of a pale yellow foam. The product is chromatographed on alumina, eluting with benzene to give about 2.3 g of 11b-(4-fluorophenyl)-1,3,4,6,7,11b-hexahydro-N,N-dimethyl-2H-benzo[a]quinolizin-2-amine as the free base. The dihydrochloride is obtained by standard procedures and then recrystallized from butanone/methanol to give 2.1 g of two different crystalline forms of 11b-(4-fluorophenyl)-1,3,4,6,7,11b-hexahydro-N,N-dimethyl-2H-benzo[a]quinolizin-2-amine dihydrochloride, m.p. 263° C. (dec.).

EXAMPLE 4

11b-(4-fluorophenyl)-1,3,4,6,7,11b-hexahydro-N,N-dimethyl-2H-benzo[a]quinolizin-2-amine A solution of 9.1 g (30.8 mmoles) of 11b-(4-fluorophenyl)-1,3,4,6,7,11b-hexahydro-2H-benzo[a]quinolizin-2-one in 100 ml of ether and 100 ml of benzene is cooled in an ice bath. 9 g (0.2 mole) of dimethylamine is bubbled into the solution. 3.0 ml (27.3 mmoles) of $TiCl_4$ in 35 ml of benzene is added dropwise with stirring under a slight positive pressure of Ar. The dark brown solution is warmed to room temperature and stirred at that temperature for one week. The reaction mixture is then poured into aqueous sodium carbonate and is extracted with ether. The extracts are dried ($MgSO_4$) and concentrated to give 10.1 g of orange oil. The oil is dissolved in 250 ml of absolute ethanol (heating required). It is hydrogenated over 1 g of 5% Pt/C. In less than 1–2 hours, 28 lbs. of $H_2$ is taken up. The product is allowed to stand overnight and is then hydrogenated for 3½ hours more. A total of 30.0 lbs. of $H_2$ is taken up (97.7% of theoretical). The mixture is filtered and the catalyst washed 3 times with ethanol. The filtrate is concentrated in vacuo to give 10.0 g of an orange oil containing some insoluble material (insoluble in benzene). The product is dissolved in dilute HCl and washed 2 times with ether. The aqueous layer is made basic with NaOH and extracted with ether. The extracts are dried (MgSO$_4$) and concentrated to give 8.2 g of 11b-(4-fluorophenyl)1,3,4,6,7,11b-hexahydro-N,N-dimethyl-2H-benzo[a]quinolizin-2-amine.

EXAMPLE 5

11b-(4-fluorophenyl)-1,3,4,6,7,11b-hexahydro-N,N-dimethyl-2H-benzo[a]quinolizin-2-amine To an ice-cold solution of 56 ml (2.16 M, 121 mmoles) of dimethyl amine in methanol is added 8 ml (5.0 N, 40 mmoles) of HCl in methanol. After 5 minutes, 5.9 g (20 mmoles) of 11b-(4-fluorophenyl)-1,3,4,6,7,11b-hexahydro-2H-benzo[a]quinolizin-2-one is added. Thereafter, 14 mmoles of NaBH$_3$CN is added. After 24 hours, some molecular sieves are added. 24 hours later, additional molecular sieves are added. After a further 24 hours, an additional 14 mmoles of NaBH$_3$CN is added. After still another 24 hours, 7.5 ml (2.16 M, 16.2 mmoles) of dimethylamine in methanol and 2.0 ml (5.0 N, 10 mmoles) of HCl are added. Three days later, the product is worked-up by pouring it into aqueous sodium carbonate and ether. The mixture is filtered through filter aid; the ether layer is washed with aqueous NaOH, brine and dried (MgSO$_4$). After concentration in vacuo, 6.25 g (96%) of a semi-oily white crystalline solid, i.e., 11b-(4-fluorophenyl)-1,3,4,6,7,11b-hexahydro-N,N-dimethyl-2H-benzo[a]quinolizin-2-amine, is obtained. This product is recrystallized from 100 ml of cyclohexane, yielding 1.6 g of 11b-(4-fluorophenyl)-1,3,4,6,7,11b-hexahydro-N,N-dimethyl-2H-benzo[a]quinolizin-2-amine, m.p. 159°–167° C.

EXAMPLE 6

11b-(4-fluorophenyl)-1,3,4,6,7,11b-hexahydro-N,N-dimethyl-2H-benzo[a]quinolizin-2-amine dihydrochloride Using the same reaction procedure as in EXAMPLE 5, 14.25 g (48.3 mmoles) of 11b-(4-fluorophenyl)-1,3,4,6,7,11b-hexahydro-2H-benzo[a]quinolizin-2-one, along with 140 ml (2.16 M, 302 mmoles) of methanolic dimethylamine, 21 ml (5.0 N, 105 mmoles) of HCl and 3.0 g (47.7 mmoles) of NaBH$_3$CN are rejected. Using the same work-up procedure as in EXAMPLE 5, 15.6 g (99%) of white crystals of 11b-(4-fluorophenyl)-1,3,4,6,7,11b-hexahydro-N,N-dimethyl-2H-benzo[a]-quinolizin-2-amine is obtained. m.p. 158°–168° C. This product is converted to the hydrochloride salt by reaction with HCl in ethanol. The salt is recrystallized from butanone/methanol, producing a highly hydroscopic HCl salt as beige needles of 11b-(4-fluorophenyl)-1,3,4,6,7,11b-hexahydro-N,N-dimethyl-2H-benzo[a]-quinolizin-2-amine dihydrochloride. After 3 subsequent recrystallizations, pink crytals are obtained. m.p. 293°–298° C. (dec.)

EXAMPLE 7

11b-(4-fluorophenyl)-1,3,4,6,7,11b-hexahydro-2-pyrrolidin-1-yl-2H-benzo[a]quinolizine dihydrochloride To an ice-cold solution of 17 ml (203 mmoles) of pyrrolidine in 50 ml of methanol is added 14 ml (5.0 N, 70 mmoles) of methanolic HCl. After about 5 minutes, 10.00 g (33.9 mmoles) of 11b-(4-fluorophenyl)-1,3,4,6,7,11b-hexahydro-2H-benzo[a]quinolozin-2-one and then 2.13 g (33.9 mmoles) of NaBH$_3$CN are added.

3 A molecular sieves are then added. The ice bath is removed and the reaction mixture is allowed to stir at room temperature, protected by a drying tube, for 2 days. The reaction mixture is worked-up as in EXAMPLE 5, giving 11.4 g of product. This is then partitioned between ether and dilute NaOH phases. The organic layer is dried (MgSO$_4$) and concentrated in vacuo. The concentrate is resubjected to modified reaction conditions, i.e., the oil is dissolved in 100 ml of methanol; 17 ml of pyrrolidine and 2.13 g of NaBH$_3$CN are added; HCl gas is then bubbled into the solution until the pH is in the range of 3–4; molecular sieves are added and the mixture is allowed to stir at room temperature for 5 days. It is then filtered through filter aid, washing several times with methanol. The filtrate is concentrated in vacuo and then partitioned between ether and dilute NaOH phases. The organic layer is extracted with dilute HCl. The acid extract is washed with ether, made basic with aqueous NaOH and extracted into ether. The ether extract is dried (MgSO$_4$) and concentrated to give 7.7 g of product. After chromatography on 350 ml of alumina, eluting with benzene, two isomers are separated. After conversion to its dihydrochloride salt, one isomer is recrystallized from butanone/methanol, yielding 11b-(4-fluorophenyl)-1,3,4,6,7,11b-hexahydro-2-pyrrolidin-1-yl-2H-benzo[a]quinolizine dihydrochloride, m.p. 279° C. (dec.). The other isomer is also converted to its hydrochloride salt and is recrystallized twice from butanone/methanol, producing 11b-(4-fluorophenyl)-1,3,4,6,7,11b-hexahydro-2-pyrrolidin-1-yl-2H-benzo[a]quinolizine dihydrochloride. m.p. 264° C. (dec.).

EXAMPLE 8

11b-phenyl-1,3,4,6,7,11b-hexahydro-N,N-dimethyl-2H-benzo[a]quinolizin-2-amine dihydrochloride A solution of 77 ml of 2.16 M dimethylamine/methanol (165 mmoles) is neutralized with HCl gas while it is cooled in an ice bath. 77 ml more of 2.16 N dimethylamine is added. This is followed by 15.3 g (55.2 mmoles) of 11b-phenyl-1,3,4,6,7,11b-hexahydro-2H-benzo[a]-quinolizin-2-one, 3.47 g (55.2 mmoles) of NaBH$_3$CN and molecular sieves. A drying tue is attached. The reaction is conducted in accordance with the details of EXAMPLE 7. The reaction mixture is then poured into dilute aqueous sodium hydroxide and ether/benzene. After stirring for about 5 minutes, the mixture is filtered through a filter aid. The organic layer is separated and the aqueous layer is extracted two times more with ether. The combined extracts are washed with water and brine and then dried (MgSO$_4$). The product is concentrated in vacuo, giving 15.6 of a soft white solid. The product is resubjected to the reaction conditions using about 500 ml of methanol as the solvent and 6 g of NaBH$_3$CN. The methanol is then removed in vacuo and the product worked-up as described above. The resultant yellow oil is dissolved in 250 ml of ice-cold ethanol and NaBH$_4$ is added. The reaction mixture is stirred at room temperature overnight. The ethanol is removed in vacuo. The residue is partitioned between ether and dilute sodium hydroxide. The aqueous layer is drawn off and the ether layer is extracted with HCl. The acid layer is washed with ether, made basic with sodium hydroxide and extracted with ether. The organic layer is washed with brine and dried (MgSO$_4$). The product is concentrated to produce 11.5 g of a pale yellow oil which is converted to the dihydrochloride salt and is recrystallized from butanone/methanol to produce 11b- phenyl-1,3,4,6,7,11b-hexahydro-N,N-dimethyl-2H-benzo[a]quinolizin-2-amine dihydrochloride.

EXAMPLE 9

11b-(4-methylphenyl)-1,3,4,6,7,11b-hexahydro-2-pyrrolidin-1-yl-2H-benzo[a]quinolizine dihydrochloride A solution of 14 ml of pyrrolidine (168 mmoles) in 75 ml of methanol is neutralized with HCl gas while the solution is cooled in an ice bath. 13 ml more (156 mmoles) of yrrolidine is added along with 100 ml of methanol. Thereafter is added 16.0 g (54.9 mmoles) of 11b-(4-methylphenyl)-1,3,4,6,7,11b-hexahydro-2H-benzo[a]quinolizin-2-one, 3.47 g (55.2 mmoles) of NaBH$_3$CN and molecular sieves. A drying tube is attached and the reaction conditions of EXAMPLE 7 are employed. The work-up procedures of EXAMPLE 8 are used to obtain 11b-(4-methylphenyl)-1,3,4,6,7,11b-hexahydro-2-pyrrolidin-1-yl-2H-benzo[a]quinolizine dihydrochloride.

EXAMPLE 10–15

Using the procedure of EXAMPLE 8, the reactants listed below are employed to form the compounds of Formula I listed below:

| Example | Amine & Corresponding Amine Hydrochloride | Ketone of Formula II $R_4$, $R_6$, $R_7$, $R_8$ = H $R_5$ | Product of Formula I |
|---|---|---|---|
| 10 | HN(CH$_3$)$_2$ | p-Cl | 11b-(4-chlorophenyl)-1,3,4,6,7,11b-hexahydro-N,N-dimethyl-2H-benzo[a]quinolozin-2-amine dihydrochloride, m.p. 275° C. |
| 11 | pyrrolidine | p-F | 11b-(4-fluorophenyl)-1,3,4,6,7,11b-hexahydro-2-pyrrolidin-1-yl-2H-benzo[a]quinolizine dihydrochloride, m.p. 279° C. |
| 12 | pyrrolidine | p-Cl | 11b-(4-chlorophenyl)-1,3,4,6,7,11b-hexahydro-2-pyrrolidin-1-yl-2H-benzo[a]quinolozine dihydrochloride, m.p. 280° C. |
| 13 | HN(CH$_3$)$_2$ | p-CH$_3$ | 1,3,4,6,7,11b-hexahydro-N,N-dimethyl-11b-(4-methylphenyl)-2H-benzo[a]quinolizin-2-amine dihydrochloride, m.p. 278° C. (dec.) |
| 14 | HN(CH$_3$)$_2$ | 4-Cl (R$_6$ = 3-Cl) | 11b-(3,4-dichlorophenyl)-1,3,4,6,7,11b-hexahydro-N,N-dimethyl-2H-benzo[a]quinolizin-2-amine dihydrochloride, m.p. 216–218° C. |
| 15 | H$_2$NCH$_3$ | p-F | 11b-(4-fluorophenyl)-1,3,4,6,7,11b-hexahydro-N-methyl-2H-benzo[a]quinolizin-2-amine dihydrochloride |

EXAMPLE 16

11b-(4-chlorophenyl)-2-ethyl-1,3,4,6,7,11b-hexahydro-2H-benzo[a]quinolizin-2-amine A solution of 7.79 g (25.0 mmoles) of 11b-(4-chlorophenyl)-1,3,4,6,7,11b-hexahydro-2H-benzo[a]quinolizin-2-one in about 125 ml of ether/tetrahydrofuran/benzene is added dropwise with stirring to a Grignard reagent prepared by adding 7.5 ml (100 mmoles) of ethyl bromide and 2.43 g (100 mmoles) of Mg to 125 ml of ether, the ether having been decanted off from any residual magnesium. The mixture is heated at reflux temperature for 18 hours. 2.43 ml of water, 2.4 ml of 15% NaOH and, then 4.8 ml of water are added. After about 1 hour, filter aid and MgSO$_4$ are added and stirring is continued overnight. The mixture is filtered through a filter aid with benzene/methylene chloride washes. It is concentrated in vacuo to give 9.0 g of product which is then dissolved in anhydrous ether and filtered through filter aid to remove insoluble material. The product is converted to the HCl salt and recrystallized from butanone/methanol (2×), to produce 11b-(4-chlorophenyl)-2-ethyl-1,3,4,6,7,11b-hexahydro-2H-benzo[a]quinolizin-2-ol hydrochloride, m.p. 222°–228° C. (dec.). The latter is then subjected to a Ritter reaction using the procedure of Krimen et al, Organic Reactions, Vol. 17, 1969, p. 213, and the reference cited therein; and subsequently is reduced to produce 11b-(4-chlorophenyl)-2-ethyl-1,3,4,6,7,11b-hexahydro-2H-benzo[a]-quinolizin-2-amine hydrochloride.

EXAMPLE 17

11b-phenyl-2-ethyl-1,3,4,6,7,11b-hexahydro-2H-benzo[a]quinolizin-2-amine

Using the procedure of EXAMPLE 16, 6.93 g (25.0 mmoles) of 1,3,4,6,7,11b-hexahydro-11b-phenyl-2H-benzo[a]quinolizin-2-one in 125 ml of tetrahydrofuran/methanol (hot) are added to the same Grignard reagent. The reaction mixture is worked-up in accordance with EXAMPLE 16 up the vacuum concentation step. Thereafter, the benzene insoluble product is filtered through a filter aid with benzene/ether. The filtrate is concentrated in vacuo to produce a light yellow oil. The filter aid is boiled with several portions of methanol and filtered. The filtrate is concentrated in vacuo and recombined with the product oil. The reaction with the Grignard reagent is repeated using tetrohydrofuran exclusively as the solvent. After work-up in accordance with EXAMPLE 16, 7.3 g of product is obtained after dissolution in benzene and filtration through a filter aid. The product is dissolved in methanol and HCl is added. The mixture is concentrated in vacuo and the solid is recrystallized from butanone/benzene (2×) to produce 2-ethyl-1,3,4,6,7,11b-hexahydro-11b-phenyl-2H-benzo[a]quinolizin-2-ol hydrochoride, hemihydrate. The latter is then subjected to a Ritter reaction using the procedure of Krimen et al, Organic Reactions, Vol. 17, 1969, p. 213 and the references cited therein; and subsequently is reduced to produce 11b-phenyl-2-ethyl-1,3,4,6,7,11b-hexahydro-2H-benzo[a]-quinolizin-2-amine hydrochloride.

EXAMPLE 18

Employing the procedure of EXAMPLE 17, except for the use of a phenyl Grignard reagent, 11b-(4-chlorophenyl)-2-phenyl-1,3,4,6,7,11b-hexahydro-2H-benzo[a]-quinolizin-2-amine hydrochloride is prepared.

EXAMPLE 19

An illustrative composition for tablets is as follows:

| | Per Tablet |
|---|---|
| (a) 11b-(4-fluorophenyl)-1,3,4,6,7,11b-hexahydro-N,N-dimethyl-2H-benzo[a]-quinolizin-2-amine | 100.00 mg |
| (b) wheat starch | 15.0 mg |
| (c) lactose | 33.5 mg |

|   | Per Tablet |
|---|---|
| (d) magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 20

An illustrative composition for a parenteral injection is the following wherein the quantities are on a weight to volume basis.

|   | Per Tablet |
|---|---|
| (a) 11b-(4-fluorophenyl)-1,3,4,6,7,11b-hexahydro-N,N-dimethyl-2H-benzo[a]-quinolizin-2-amine dihydroxhloride | 100.0 mg |
| (b) sodium chloride | q.s. |
| (c) water for injection to make | 20 ml |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 21

An illustrative composition for hard gelatin capsules is as follows:

|   | Amount |
|---|---|
| (a) 11b-(4-fluorophenyl)-1,3,4,6,7,11b-hexahydro-N,N-dimethyl-2H-enzo[a]-quinolizin-2-amine | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 22

An illustrative composition for pills is the following:

|   | Per Pill |
|---|---|
| (a) 11b-(4-fluorophenyl)-1,3,4,6,7,11b-hexahydro-N,N-dimethyl-2H-benzo[a]-quinolizin-2-amine | 200 mg |
| (b) corn starch | 130 mg |
| (c) liquid glucose | 20 ml |

The pills are prepared by blending the active ingredient (a) and the corn starch; then adding the liquid glucose with thorough kneading to form a plastic mass from which the pills are cut and formed.

We claim:

1. A compound of the formula

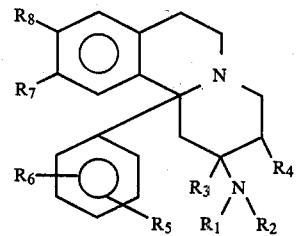

wherein
$R_1$ is hydrogen, a straight or branched chain alkyl of 1-5 carbon atoms or a straight or branched chain alkanoyl of 1-5 carbon atoms;
$R_2$ is hydrogen, a straight or branched chain alkyl of 1-5 carbon atoms, phenyl, phenyl substituted with halogen, a straight or branched chain alkoxy of 1-5 carbon atoms, a straight or branched chain alkyl of 1-5 carbon atoms or trifluoromethyl or, when $R_1$ is hydrogen, $R_2$ can also be straight or branched chain alkanoyl of 1-5 carbon atoms; or
$R_1$ and $R_2$ taken together with the nitrogen atom to which they are attached are azetidine, pyrrolidine, piperidine, hexahydroazepine, morpholine or piperazine;
$R_3$ is hydrogen, primary or secondary alkyl of 1-5 carbon atoms, phenyl or phenyl substituted by halogen, a straight or branched chain alkoxy of 1-5 carbon atoms, a straight or branched chain alkyl of 1-5 carbon atoms or trifluoromethyl;
$R_4$ is hydrogen or a straight or branched chain alkyl of 1-5 carbon atoms;
$R_5$ is 4-fluoro;
$R_6$ is hydrogen; and
each of $R_7$ and $R_8$ is hydrogen;
or a pharmaceutically acceptable acid addition salt thereof.

2. 11b-(4-Fluorophenyl)-1,3,4,6,7,11b-hexahydro-N,N-dimethyl-2H-benzo[a]quinolizin-2-amine, a compound of claim 1.

* * * * *